United States Patent
Greenfield

Patent Number: 6,050,264
Date of Patent: Apr. 18, 2000

[54] LARYNGEAL MASK ASSEMBLIES

[75] Inventor: Brian George Greenfield, Sellindge, United Kingdom

[73] Assignee: Smiths Industries Public Limited Company, London, United Kingdom

[21] Appl. No.: 08/924,636

[22] Filed: Sep. 5, 1997

[30] Foreign Application Priority Data

Sep. 18, 1996 [GB] United Kingdom .................. 9619432

[51] Int. Cl.⁷ ................................................. A61M 16/00
[52] U.S. Cl. .............................. 128/207.15; 128/207.14; 128/200.26
[58] Field of Search ........................ 128/200.26, 207.14, 128/207.15, DIG. 26

[56] References Cited

U.S. PATENT DOCUMENTS

| | | |
|---|---|---|
| 4,995,388 | 2/1991 | Brain . |
| 5,241,956 | 9/1993 | Brain . |
| 5,249,571 | 10/1993 | Brain . |
| 5,273,029 | 12/1993 | Wilk et al. ................ 128/200.26 |
| 5,282,464 | 2/1994 | Brain . |
| 5,297,547 | 3/1994 | Brain . |
| 5,303,697 | 4/1994 | Brain ................ 128/200.26 |
| 5,305,743 | 4/1994 | Brain . |
| 5,355,879 | 10/1994 | Brain . |
| 5,477,851 | 12/1995 | Callaghan et al. . |
| 5,546,937 | 8/1996 | Stuart et al. ............... 128/207.15 |
| 5,632,271 | 5/1997 | Brain ............... 128/207.15 |
| 5,682,880 | 11/1997 | Brain ............... 128/207.15 |
| 5,771,889 | 6/1998 | Pagan ............... 128/207.15 |
| 5,791,341 | 8/1998 | Bullard ............... 128/207.15 |

FOREIGN PATENT DOCUMENTS

| | | |
|---|---|---|
| 0 448 878 | 10/1991 | European Pat. Off. . |
| 2111394 | 7/1983 | United Kingdom . |
| 2128561 | 5/1984 | United Kingdom . |
| 2249959 | 5/1992 | United Kingdom . |
| 2259454 | 3/1993 | United Kingdom . |
| 2267034 | 11/1993 | United Kingdom . |
| 2294642 | 5/1996 | United Kingdom . |

*Primary Examiner*—John G. Weiss
*Assistant Examiner*—Todd M. Martin
*Attorney, Agent, or Firm*—Pollock, Vande Sande & Amernick

[57] ABSTRACT

A laryngeal mask assembly has a laryngeal mask device with a tube opening into a mask. The assembly includes an obturator inserted along the tube during insertion, with the patient end of the obturator lying adjacent the patient end of the tube so as to prevent the epiglottis entering the tube. The obturator has an air passage extending along its length and a handle projecting rearwardly from a stop, which limits how far the obturator can be inserted in the tube.

1 Claim, 1 Drawing Sheet

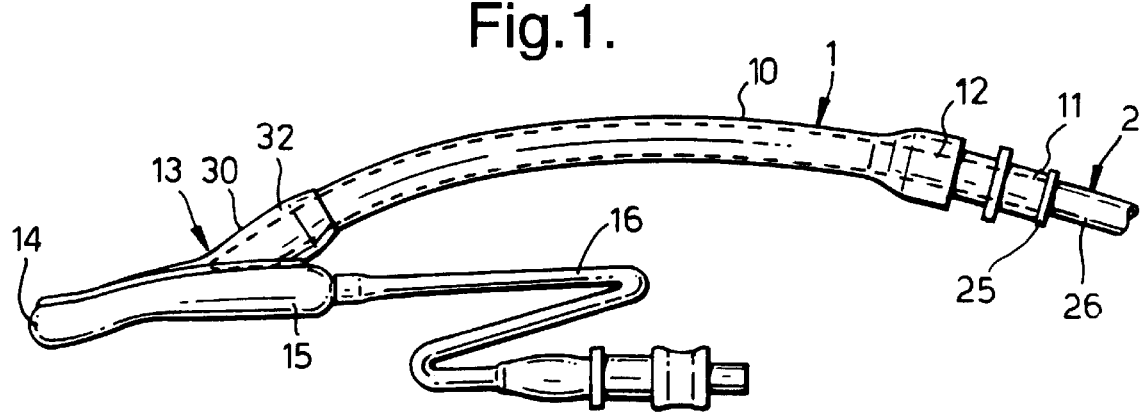
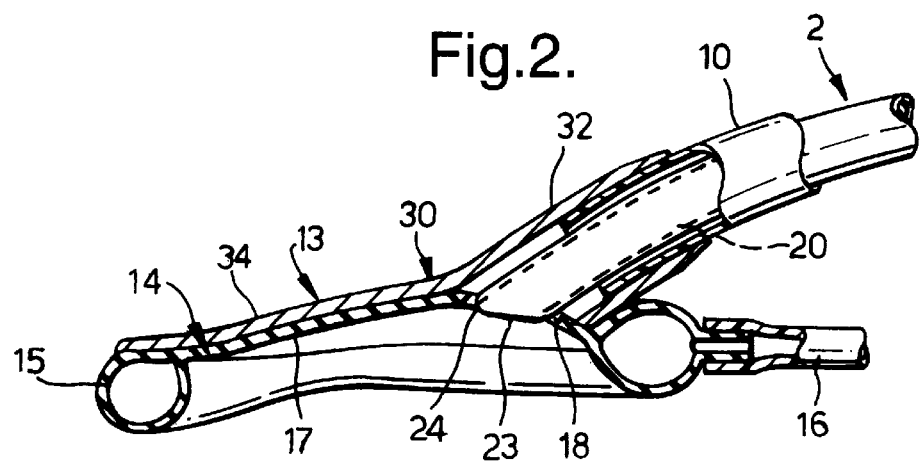

LARYNGEAL MASK ASSEMBLIES

BACKGROUND OF THE INVENTION

This invention relates to laryngeal mask assemblies.

It is common practice to use airways known as laryngeal masks for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. No. 5,355,879, U.S. Pat. No. 5,305,743, U.S. Pat. No. 5,297,547, U.S. Pat. No. 5,282,464, GB 2267034, U.S. Pat. No. 5,249,571, U.S. Pat. No. 5,241,956, U.S. Pat. No. 5,303,697, U.S. Pat. No. 5,477,851, GB 2249959, GB 2111394, EP 448878, U.S. Pat. No. 4,995,388, GB 2205499, GB 2128561, GB2294642 and GB 2298797.

Introducers have also been described, such as in GB 2259454, in which the introducer is placed in the patient's mouth and the laryngeal mask is slid along a channel in the introducer.

Laryngeal masks have several advantages over endotracheal tubes, which are longer and seal with the trachea below the vocal folds. Laryngeal masks do, however, have several problems. It is possible, for example, during insertion, for the epiglottis to enter and block the bore of tube. One solution to this is to place flexible cross bars at the patient end of the tube, in the manner described in GB 2205499. This, however, involves an obstruction at the patient end of the tube, which may be undesirable.

Another problem arises from the fact that the tube must be sufficiently soft and flexible, in order to conform to the anatomy and be atraumatic, yet a certain amount of force is needed to introduce the mask assembly to the correct position. One method of insertion of the mask is to slide its tip against the soft palate as it is introduced, in order to stimulate a swallowing action while preventing a retching reflex. In order to do this, the clinician has to hold the tip of the mask against the soft palate with his finger, pushing his finger into the patient's mouth to its full extent, as the mask is inserted. Clinicians with smaller hands can have difficulties with this procedure. Another problem arises from the soft nature of the tube, in that it is prone to bend and twist during insertion, making it difficult to position correctly.

BRIEF SUMMARY OF THE INVENTION

It is an object of the present invention to provide an improved laryngeal mask assembly and a method of inserting a laryngeal mask device of the kind comprising a mask and an elongate tube that opens at its patient end into said mask.

According to one aspect of the present invention there is provided an assembly including a laryngeal mask device having an elongate tube that opens at its patient end into a mask adapted during use to locate in the hypopharynx, the mask opening on its forward side to the patient's airway, the assembly including an obturator insertable within the tube, and the obturator being arranged during insertion of the assembly to extend along the length of the tube with the patient end of the obturator being located adjacent the patient end of the tube so as to prevent entry of the epiglottis into the patient end of the tube during insertion of the assembly.

The obturator preferably has an air passage extending along its length. The obturator may be provided with a stop towards its machine end to limit the extent of insertion of the obturator into the tube. The obturator may extend rearwardly beyond the stop to form a handle by which the assembly can be manipulated.

According to another aspect of the present invention there is provided an obturator when used in assembly according to the above one aspect of the invention.

A further aspect of the invention is a method of inserting a laryngeal mask device of the kind comprising a mask and an elongate tube that opens at its patient end into said mask, comprising the steps of: inserting an obturator into said tube so that a patient end of said obturator is located adjacent a patient end of said tube; inserting an assembly of said laryngeal mask device and said obturator into a patient so that said mask locates in the patient's hypopharynx and opens on its forward side to the patient's airway; and subsequently removing said obturator while leaving said laryngeal mask device in position.

A laryngeal mask assembly and its method of use, according to the present invention, will now be described, by way of example, with reference to the accompanying drawing.

BRIEF DESCRIPTION OF THE DRAWING

FIG. 1 is a side elevation view of the assembly; and

FIG. 2 is an enlarged sectional side elevation view of the patient end of the assembly.

DETAILED DESCRIPTION OF THE PREFERRED EMBODIMENTS

The assembly comprises a laryngeal mask device 1 and an obturator 2 inserted within the mask device.

The mask device 1 has a bendable tube 10 of a plastics material, such as PVC, with a coupling 11 at its machine end 12. The tube 10 is curved along its length and is joined at its patient end to a mask subassembly 13 comprising a mask portion 14 and a mount 30, as described in detail in U.S. Pat. No. 5,771,889. The mask portion 14 has a peripheral annular sealing ring 15 connected with an inflation line 16 by which the ring can be inflated and deflated with air. The sealing ring 15 is of elliptical shape with its major axis extending in the same plane as the tube 1. Within the ring 15, the mask portion has a flexible diaphragm 17 with a shallow conical shape. An opening 18 in the diaphragm 17 communicates with the bore through the tube 10.

The mount 30 has a short tubular extension 32 extending a short distance along the outside of the machine end of the tube 10 and is sealed with it by means of welding, solvent or an adhesive. The patient end of the tubular extension 32 is aligned with the opening 18 in the diaphragm 17. The mount 30 is completed by a backing plate 34 formed integrally with the tubular extension 32, which forms an extension of the tube 10. The backing plate 34 is of generally elliptical shape and extends forwardly from the patient end of the tubular extension. The lower, forward side of the backing plate 34 is secured to the upper, rear surface of the diaphragm 17 and overlaps the sealing ring 15 at the patient end or tip. There are various other ways in which a mask portion can be attached to the patient end of the tube 10.

The obturator 2 is of a stiff but bendable plastics material and is of tubular form pre-curved to the shape of the tube 10, having an external diameter slightly less than the internal diameter of the tube so that it is a sliding fit within the tube. The obturator 2 has a bore 20 extending through it and providing an air passage along the obturator. The diameter of the bore 20, at least at the patient end of the bore, is selected to be small enough to prevent entry of the epiglottis. The patient end 23 of the obturator 2 may be provided with cross bars to prevent entry of the epiglottis while enabling the bore 20 to be as large as possible. The forward, patient end 23 of the obturator 2 is preferably bevelled, so that it lies substantially coplanar with the diaphragm 17, and has a rounded, atraumatic edge 24. A flange 25 or similar stop on the exterior of the obturator 2 towards its machine end limits the extent of insertion by engaging the connector 11, or the end of the tube 10 if there is no connector. The rear, machine end of the obturator 2 extends a short distance beyond the flange 25 to form a handle 26 by which the assembly can be manipulated. When the obturator 2 is fully inserted, with the flange 25 abutting the connector 11, the patient end 23 of the obturator is located level with, or projects slightly beyond the aperture 18.

The obturator 2 gives the tube 10 additional stiffness during use. This helps prevent the tube twisting and bending during insertion but enables it to retain its flexibility after removal. The increased stiffness of the assembly enables the clinician to push the tip of the mask device 1 against the patient's soft palate during insertion by gripping the machine end of the assembly and without the need to insert his finger into the patient's mouth. When the assembly slides past the epiglottis, the patient end 23 of the obturator 2 ensures that the epiglottis does not enter the patient end of the tube 10. After insertion, the obturator 2 is removed and the sealing ring 15 is inflated, in the usual way.

Various modifications can be made to the obturator. The obturator could be stiffened in various ways. For example, reinforcing rods or layers could be coextruded within its wall, or a spiral or braid reinforcement could be used. The lumen of the obturator could be shaped to increase its stiffness or to give it preferential stiffness in selected planes. The handle 26 need not be a straight continuation of the main part of the obturator, instead, it could be bent at an angle or provided as a T-bar. The handle may incorporate a connector to enable connection to a ventilator. The patient end of the obturator may have a Moore taper and Murphy eyes. The obturator may be adapted to provide for endoscope tracheal examination, such as by the incorporation of a fibre-optic guide or a lumen along which an endoscope can be inserted. The bore through the obturator may be shaped to enable insertion of a tracheal tube or suction catheter. The patient end of the obturator may have an extension of spatula shape on the outer side of its curvature, which projects into the trachea and lies along the wall of the trachea on the side remote from the throat. The purpose of the extension is to serve as a guard to protect the underlying wall of the trachea from trauma during the insertion of a percutaneous tracheostomy tube.

What I claim is:

1. A method of inserting a laryngeal mask device comprising a mask and an elongate tube that opens at a patient end of said tube into a hollow recess on a forward surface of a support of said mask surrounded by an inflatable cuff, comprising the steps of: inserting an obturator into said tube so that a patient end of said obturator is located adjacent said patient end of said tube without protruding substantially therefrom, the dimensions of the patient end of the obturator being such as to prevent entry of the epiglottis into a bore at the patient end of the tube during insertion of the laryngeal mask device into a patient; inserting an assembly of said laryngeal mask device and said obturator into a patient so that said obturator engages and deflects the epiglottis during said inserting, said mask locates in the patient's hypopharynx and opens on a forward side to the patient's airway; and subsequently removing said obturator while leaving said laryngeal mask device in the patient's hypopharynx.

* * * * *